Figure 1:
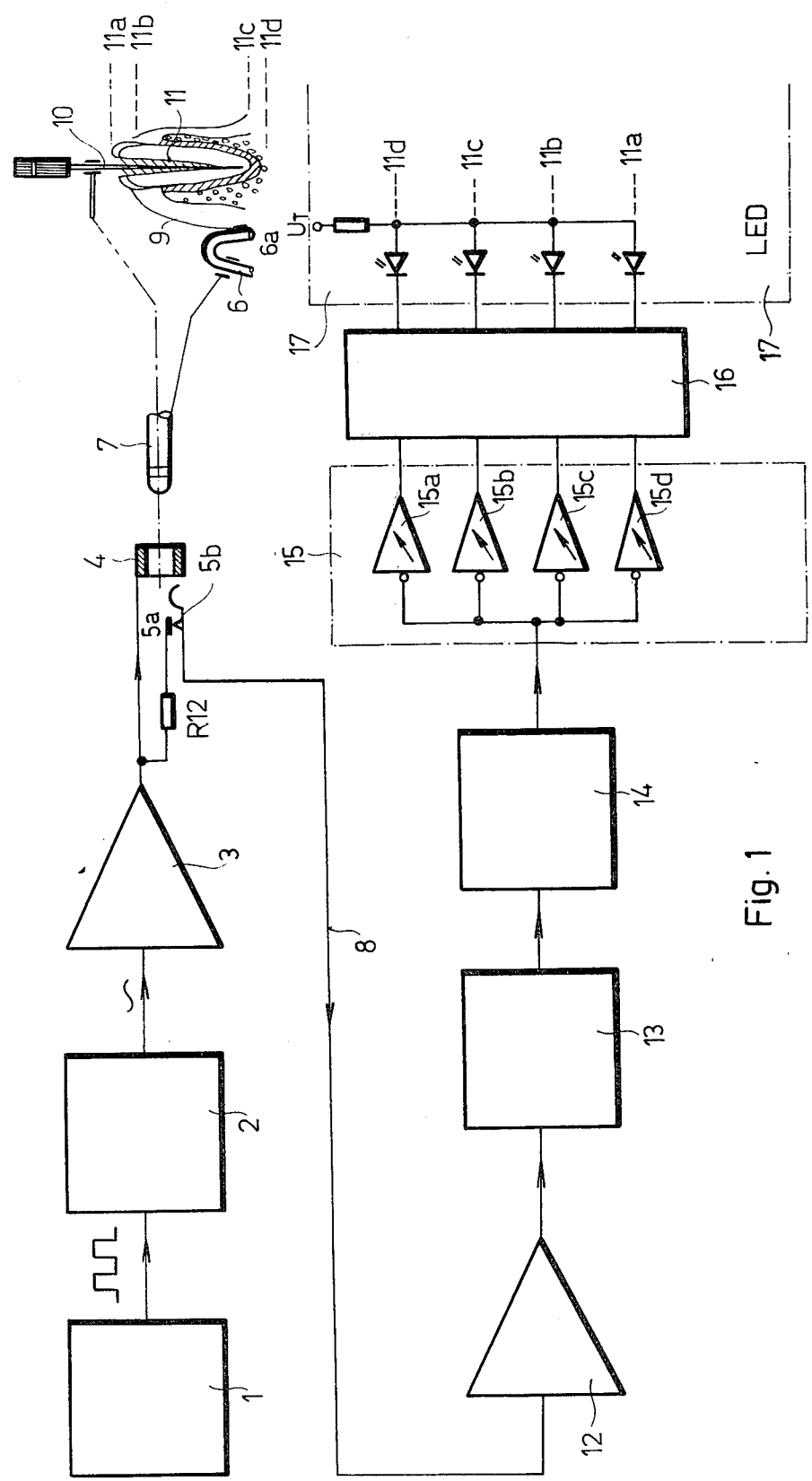

United States Patent [19]

Déry et al.

[11] 4,353,693
[45] Oct. 12, 1982

[54] APPARATUS FOR THE DETERMINATION AND THE DIGITAL DISPLAY OF THE POSITION OF ROOT TREATING MEANS IN THE TOOTH

[76] Inventors: Tibor Déry, 12, Fehérhajó utca, 1052 Budapest; Attila Madocsay, 5, Tárnok utca, 1014 Budapest, both of Hungary

[21] Appl. No.: 150,409

[22] Filed: May 13, 1980

[30] Foreign Application Priority Data

May 14, 1979 [HU] Hungary ............................... DE 994

[51] Int. Cl.³ .............................................. A61C 3/00
[52] U.S. Cl. ....................................... 433/27; 433/75; 433/224; 433/91; 128/776
[58] Field of Search ...................... 433/75, 72, 32, 224, 433/27, 91; 33/174 D; 128/774, 776, 777

[56] References Cited

U.S. PATENT DOCUMENTS

| | | | |
|---|---|---|---|
| 3,058,225 | 10/1962 | Ward | 33/174 D |
| 3,753,434 | 8/1973 | Pike et al. | 128/776 |
| 3,916,529 | 11/1975 | Mousseau | 33/174 D |
| 3,993,044 | 11/1976 | McGuffin | 433/224 |
| 4,192,321 | 3/1980 | Korber et al. | 128/776 |
| 4,193,408 | 3/1980 | Fujino | 128/776 |
| 4,197,641 | 4/1980 | Paulke et al. | 433/32 |
| 4,215,698 | 8/1980 | Nuwayser | 128/776 |
| 4,243,388 | 1/1981 | Arai | 433/224 |

*Primary Examiner*—Gene Mancene
*Assistant Examiner*—John J. Wilson
*Attorney, Agent, or Firm*—Young & Thompson

[57] ABSTRACT

Apparatus for the determination and the digital display of the position in the tooth canal of a root treating device, comprises a saliva suction device in circuit with the root treating device to sense the variation of the impedance between the gum and the root treating device. That impedance varies inversely as the depth of the root treating device; and so the variations in impedance are amplified and converted into DC voltage levels which are applied to a series of light displays in such a way that one light display will be most brightly illuminated while its neighbors will be less brightly illuminated, the comparative illuminations of the adjacent light displays giving a quick visual indication of the position of the root treating device in the tooth canal. An audible signal can also be provided.

4 Claims, 3 Drawing Figures

APPARATUS FOR THE DETERMINATION AND THE DIGITAL DISPLAY OF THE POSITION OF ROOT TREATING MEANS IN THE TOOTH

The object of the invention is an apparatus for the determination and the digital display of the position in the tooth channel of root treating means used in dental practice.

One of the most important operations of the dentist's work and the most important task in treating the root is the exposure of the cavity occupied by the dental pulp and the length of the root channels completely. But the examination with the required accuracy of the root channels to this effect by roentgenology proved not viable due to variations in the projection and the anatomy.

Important operations before the final stopping of the root channels for their sterilization are the cleaning (probing) of the root channel, the removal of the inflamed tissues and the widening of the root channel and the tip aperture. The destructions, overdilatations, the injuries afflicted to the tissues around the stopping, etc., which may be caused by mechanical root treatment means may necessitate in certain cases the removal of the tooth unavoidably. An obvious solution of determining the length of the root channel was seemingly the use of the mechanical root treating means as measuring instruments. One of the first solutions consisted of introducing the needle into the root channel until its point reached the root tip, then pulling it out by forceps supported on the masticatory surface of the tooth and measuring it; as a newer solution a rubber disc or a stop was pulled on the root treating needle, deepened for the first time up to the root tip and determining the distance between the point of the needle and the impact ring, based on the position corresponding to its usage, also for the subsequent operations (see the textbook by Adler-Záray-Bánóczy: "Cariologia and endodentia", Budapest, 1978, pp. 286–87). But these measurements are circumstantial and fail to supply accurate values.

Apparatuses are known from the literature, by which the position of the root treating means introduced into the root channel may be determined on the basis of the variation of the conductivity of the tooth material and the ohmic resistance between it and the means. The operating principle of these apparatuses is that the conductivity of the tooth material, whose value is relatively constant at the root tip, varies proportionally with the penetration depth of the means related to the root tip. The variation of the resistance is indicated by a pointer-scale instrument. The dead tooth pulp shows a higher resistance than the live one, but the deviating indications of the pointer due to this phenomenon may be evaluated only subjectively, by comparison or estimation and supply no accurate data for the length of the channels, or for the variations of the tooth cavities occupied by the pulp.

In addition to their listed disadvantages the methods and apparatuses mentioned above cannot ensure the complete elimination of the risks connected with the root treatment operations either.

The aim of the invention is, beside the elimination of the listed disadvantages, to facilitate the evaluation of the measurement results and to eliminate the subjective reading inaccuracies of the known apparatuses by indicating not alone the length of the root channel, but also the position of the point of the dilating means used for the root treatment relative to the root tip in the various anatomical sections of the root channel, in digital form, in several stages, only during the passage of the needle point through the corresponding section.

The solution according to the invention utilizes the known principle of measuring the A.C. conductivity, developing it further by replacing the display apparatuses known so far by various LED lighting diodes for indicating the penetration depth of the root treating needle at intervals based on the various conductivities belonging to the corresponding anatomical sections, with the help of an appropriate peak rectifier, amplifier, a comparator and decoding circuits.

The essence of the invention is that after the peak rectifier a D.C. voltage representing the penetration depth of the root treating instrument is applied to the inputs of comparators, or amplifiers, adjusted to the upper limit voltage levels of the sections, whose number corresponds to that of the anatomical sections to be displayed, and whose outputs are applied to the corresponding inputs of a digital integrated decoding circuit and so the subsequent output voltages of the comparators switch on always one and only one lighting LED diode at the output of the peak detecting circuit, indicating unequivocally that the point of the root treating needle is on the root tip, or in the anatomical range preceding it, or beyond it.

The invention and its implementation form illustrated as an example in the attached drawings, is described in more detail below. In the drawings FIG. 1 is a block scheme showing the operation of the apparatus, FIG. 2 shows the arrangement of the circuitry of the apparatus, and FIG. 3 is a view similar to that of FIG. 2 but showing another embodiment of the invention.

The signal of the square generator 1 is converted by the high stop filter 2 into a sinusoid signal, then the connection jack socket of the meter 4 is connected to the low output impedance driving amplifier 3 and the lead section between both is connected also—through the inserted calibrated resistor R12, to the switch-contactor 5a. Into the socket 4 the jack plug 7, connected with the saliva suction device 6, may be plugged and fixed in an elastic way by the extension of line 8 of the switch-contactor 5b. The saliva suction device applies the signal over the contacting surface 6a, through a low impedance to the gum 9 and this signal is sensed during the introduction of the root treating means 10 into the tooth channel 11 to various depths through various impedances. The varying impedance influences the gain factor of the receiving amplifier 12 through the line 8 of the switch-contactor 5b, whereby a nearly sinusoid signal of varying amplitude is generated on the output of the amplifier and this signal is inverted into a D.C. voltage level corresponding to the amplitude of the signal. This D.C. voltage is applied, through the sectioning amplifier 14 of a suitably high input impedance and a low output impedance to four various amplifiers of sequentially decreasing gains, or comparators of sequentially increasing tilting levels 15, corresponding to the impedance limits of the anatomical sections involved by the penetration of the root treating means 10 into the tooth channel 11. The tooth treating means 10 may be dilators, files, needles, or reamers used in the dentistry profession, operated manually or mechanically.

The output voltages of the amplifiers, or comparators are converted by the influence of the increasing input D.C. voltage levels to subsequent stepwise low logic levels. The outputs 15a, 15b, 15c and 15d of the comparator 15 are applied to the corresponding inputs of the digital decoding circuit 16, preferably a BCD-decimal decoder, from whose outputs only one output controls, according to the combinations of the low input logic levels, the light displays of the LED lighting diodes 17 connected to it.

Figure 2:
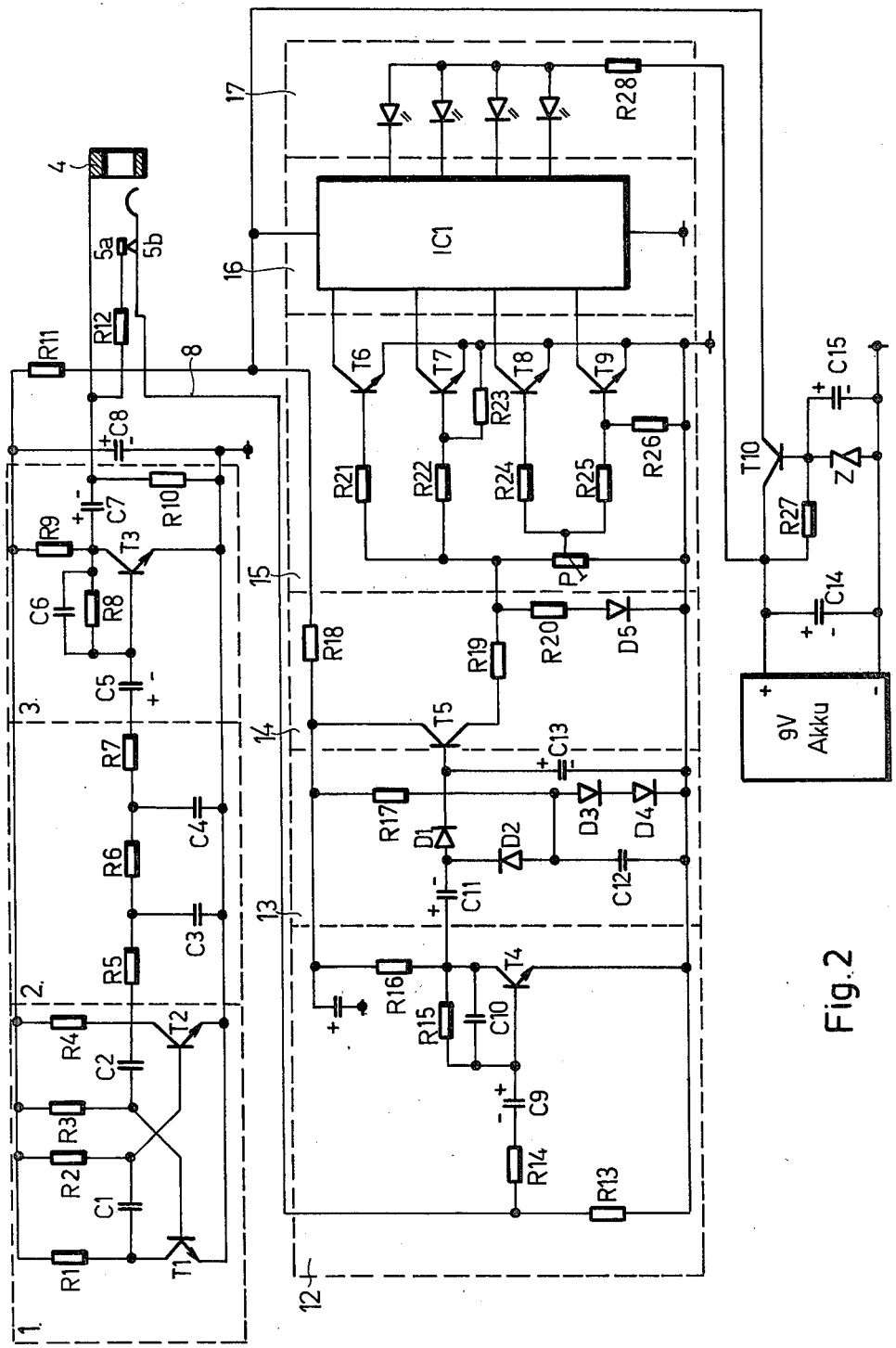
Figure 3:
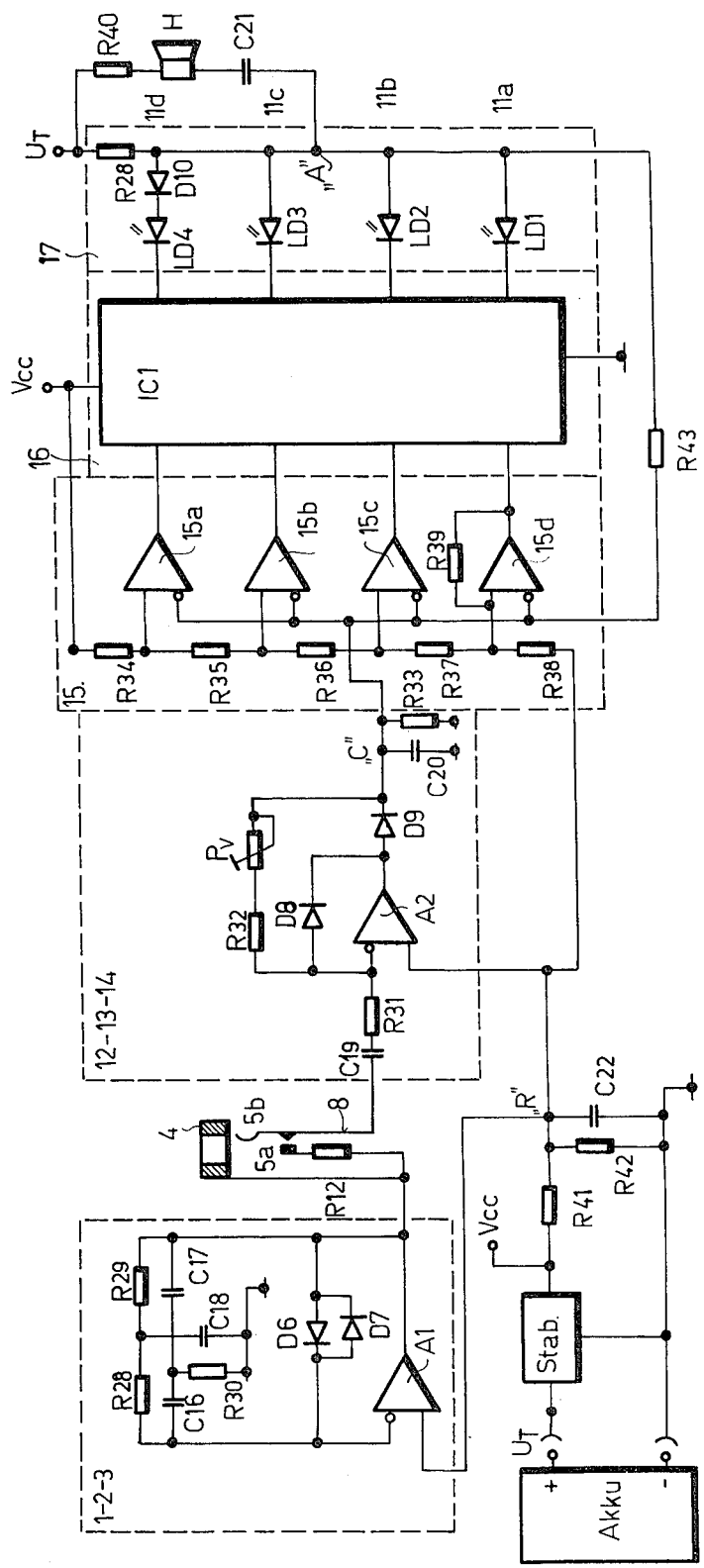

In the connection scheme shown in FIG. 2 of another implementation example of the apparatus the units presented in the block scheme are delimited by dashed lines and carry the same numbering. From the description of the figure the operation and the use of the instrument may be learned.

In block 1 the unstable multivibrator generates a square wave signal, which is applied through the filter chain 2 and the driving amplifier 3 in a closely sinusoidal form to the jack connection socket 4 of the measuring line and through the calibrated resistor R12 to the contactor 5a. Without plugging the measuring line the contactors 5a and 5b are connected in the closing sense, so the voltage of a stable amplitude found on the collector of the driving transistor T3 results in the current determined by the resistors R12 and R14 on the basis of the transistor T4 of the receiving amplifier 4.

On plugging the jack plug 7 connecting the measuring line of the root treating means 10 the closed state of the contactors 5a and 5b ceases and the measuring current flows according to the block scheme through the saliva suction 6, the gum and the conducting material of the dilator needle of the tooth channel 11, or of the root channel treating means 10 and the line 8 to the transistor T4.

The conductivity of the above current path is determined decisively by the position of the root treating dilator needle 10 in the root channel 11 of the tooth relative to the root tip.

The value of the resistor R12 is adjusted to the resistance value, which may be measured between the saliva suction device 6 and the root treating needle in the position of the point of the root treating dilator needle 10 reaching just the root tip accurately. Thereby the sensitivity and the display of the apparatus may be calibrated directly to the root tip position.

From the collector of the transistor T4 a sinusoidal voltage is applied to the peak-to-peak rectifier 13 consisting of the diodes $D_1$, $D_2$ and the capacitor $C_{13}$, whence the generated D.C. voltage is led through the transistor T15 of the high input impedance and low output impedance separation amplifier 14 to the set of amplifiers used as comparator 15.

The base currents of the transistors T6, T7, T8, T9 are adjusted by the emitter voltage of the transistor T5 through the resistors R19, R21, R22, R23, P, R24, R25, R26 by controlling the transistors in the order of the increasing voltage into opening, which then switch the corresponding inputs of the BCD-decimal decoding circuit 16 connected to their collectors in the given sequence to the ground, i.e. to a low logic level.

The transistors T6, T7, T8 and T9 switch over to the inputs of the binary digit positions $2^3$, $2^0$, $2^1$ and $2^2$ respectively of the decoding circuit.

From the ten outputs only four are used, by which the cathode of only one LED lighting diode 17 is switched to the ground at the corresponding codes of the inputs. The utilized outputs are those of the digit positions 7, 6, 4, 2.

The instrument according to the invention may be operated by a 9V supply source of digital display, it may be powered by a battery permitting to measure 40-50 channels safely without replacing the set. The actual reliable measurement at all times is ensured by a calibrating circuit with the help of the resistor R12 adjusted to the appropriate value, switched off automatically, when the measuring line 8 is connected to it. It operates at the frequency of 300 Hz, with a measuring current of 0.5 mA and a measuring voltage of 1-2V, which is not harmful to the living tissues and is not even sensed.

So the measurement is fully objective, the cooperation of the patient is not necessary. One of the measuring leads is connected in an easily releaseable manner to the root treating means 10, e.g. a Kerr-type dilator.

The other electrode is nipped to the saliva suction device 6. The digital display facilitates the evaluation of the measurement result greatly. The tooth pulp cavity 11 is divided into four ranges, according to the penetration depths denoted by 11a, 11b, 11c and 11d, resp. from the aspect of the resistance values.

Accordingly four light emitting diodes (LED) indicate the position of the point of the root treating means 10 relative to the root tip. The first green LED diode indicates the penetration depth 11a of the point (the field of the cavum pulpae), which is short, corresponding to an advance of 1-1.5 mm of the electrode (75-58 kOhm). The next green light indicates the penetration depth 11b, which is the full length of the channel (canalis pulpae), i.e. 12-25 mm, depending on the length of the tooth (58-6.5 kOhm). Reaching the root tip (apex) 11c is indicated by a red light signal. This is a very short range of 0.1-0.2 mm (6500 Ohm). When the root treating means passes the level 11c (apex) and reaches the level 11d under the root tip perispicalis region), the yellow diode indicates it.

The apparatus may be used, after calibration for routine root filling (e.g. by paste, compressed gutta-percha), so the use of the instrument means no surplus work whatever FIG. 3 shows another example of the implementation form of the invention, where the passage of the root treating means over the fields 11c and 11d of the root tip is indicated beside the red light signal (LED) also by an accompanying sound signal of variable intensity and if the jack connection plug 7 is plugged in, e.g. in the case of a pair of measuring lines suspended in the air, a warning signal is given by the flashing of the LED diode LD1 and a low frequency sound signal.

On the basis of FIG. 3 the operation of the circuit may be followed as described below: The circuit functions realized by the blocks 1, 2, 3 and 12, 13, 14 in FIGS. 1 and 2 are performed according to FIG. 3 combined by the double T sine-oscillator denoted 1-3 and the low time constant positive peak rectifier amplifier denoted 12-14.

The block 1—3 is a sine-oscillator realized by the operation amplifier A1 and the double T-feedback (R28, R29, B30, $C_{16}$, $C_{17}$, $C_{18}$). The amplitude of the oscillator is stabilized by the diodes $D_6$, $D_7$. The sinusoidal measuring voltage is led from the low impedance output of the operation amplifier A1 to the jack connection socket 4 of the measuring line and through the calibration resistor $R_{12}$ to the contactor 5a. Without plugging the measuring line the contactors 5a and 5b are connected in the closing sense, so that stable amplitude voltage on the output of the operation amplifier A1 results in the current determined by the resistors R12 and R31 on the inverting input of the operation amplifier A2 of the low time constant, positive peak rectifier-amplifier block denoted 12–14.

Upon plugging the jack plug 7 connecting the measuring line of the root treating means 10 the closed state of the contactors 5a and 5b ceases and the measuring current flows according to the block scheme through the saliva suction device, the gum, the conducting material of the dilator needle of the tooth channel 11, or root channel treating means 10 and the line 8 to the inverting input of the operation amplifier A2.

The conductivity of the above current path is determined decisively by the position of the extender needle of the root treating means 10 in the root channel 11 of the tooth relative to the root tip.

The value of the resistor $R_{12}$ is adjusted to the resistance value, which may be measured between the saliva suction 6 and the root treating needle, when the point of the dilator needle of the root treating means 10 reaches exactly the root tip, whereby the sensitivity and the display of the apparatus may be calibrated directly to the root tip position by the adjusting resistor $R_{32}$ and $P_v$ connected to the negative feedback of the operation amplifier A2. The circuit of the operation amplifier A2 functions—with the diodes $D_8$, $D_9$ and the capacitor $C_{20}$ connected to it appropriately,—as a positive peak rectifier circuit. At point "C" of the capacitor $C_{20}$ related to the reference voltage point "R" of the resistance divider $R_{41}$ and $R_{42}$ a D.C. voltage corresponding to the peak value of the positive half wave of the measured sine-wave is generated, which is led directly to the high input impedance inverting input of the integrated comparator circuits 15. The non-inverting inputs of the individual comparators are connected to the points of increasing voltages of the resistance divider $R_{34}$, $R_{35}$, $R_{36}$, $R_{37}$, $R_{38}$. The individual members of the resistance divider are adjusted to the voltage levels obtained in the boundary point "C" of the an atomical sections to be displayed, when the point of the root treating instrument reaches it in the tooth channel.

The outputs of the comparators denoted 15a, 15b, 15c, 15d switch the corresponding inputs of the BCD-decimal decoding circuit in sequence to the ground, i.e. a low logic level.

The outputs of the comparators 15a, 15b, 15c and 15d are connected to the binary digit positions $2^3$, $2^0$, $2^1$ and $2^2$ respectively of the decoding circuit.

From among the ten outputs only four are used for switching the cathode of only a single LED lighting diode 17 each time at the correspondidng codes of the inputs to the ground.

The utilized outputs are the decimal digit positions 7, 6, 4, 2. Parallelly with the resistor $R_{28}$ drawing the display diodes LD1, LD2, LD3 and LD4 to the supply voltage and in series with the resistors $C_{21}$ and $R_{40}$ a sound emitting means denoted H, preferably a small size loudspeaker is connected. The time constant formed by the capacitor $G_{20}$ of the peak rectifier and the resistors $R_{32}$, $P_v$ and $R_{33}$ is adjusted in such a way that between two subsequent period peak values at the sine oscillator frequency of the block 1–3 a slight voltage drop appears, whereby a D.C. voltage modulated by a low amplitude saw-tooth signal is obtained at the inut point "C" of the comparators. In this way the switch-over is modulated according to the frequency of the sine oscillator near to the switch-over voltage levels of the comparators 15a, 15b, 15c, 15d, so the display lighting diodes are switched over from one level to another virtually by the dimming of the light of one and the intensifying of the light of the other one, as a measure of the decreasing, or increasing space factor of the square signals controlling the switching of the adjacent LED diodes on the output of the BCD-decimal decoding circuit, attained at the varying level-transitions of the modulating saw-tooth signal.

The switch-over between two LED diodes upon passed over a comparation level is extraordinarily fast, so a sound is formed in the loudspeaker H only, when after the level is passed also the voltage level at point "A" is changing. The opening voltage of the identical type (green) LED diodes LD1 and LD2 is identical, so the switch-over is not accompanied by a sound phenomenon.

The opening voltage of the (red) LED diode LD3 is lower by about IV than that of the LED diode LD2, therefore when the level is passed at 11c, a sound of a frequency equalling that of the sine oscillator block 1–3, with a pulse width modulated according to the penetration depth and so of a corresponding sharpness is formed in the loudspeaker. H.

The opening voltage of the (yellow) LED diode LD4 is higher by about IV than that of the diode LD3, simultaneously at the level passed in 11d the voltage jump formed at point "A" and along with it the sound intensity in the loudspeaker H is increased also by the opening voltage of the diode D10, connected in series with the LED diode LD4. Point "A" joins by the high value resistor $R_{43}$ the point C and the comparator 15d is positively fed back by the resist or $R_{39}$. So when the apparatus is switched on and the jack plug 7 is plugged in, before the penetration position 11a of the point of the dilator needle of the root treating means 10 the voltage at point "C" is lower than the comparation voltage switched to the common point of the comparator 15d, the resistors $R_{37}$, $R_{38}$, at a measured impedance of practically over 75 kOhm. Thereby the value of the voltage at point "A" is close to $U_T$, as none of the LED diodes is switched on. The capacitor C20 is charged up to the switching voltage level of the comparator 15d through the resistor $R_{43}$ and after it is attained, it switches the output of the BCD-decimal decoding circuit connected to the diode LD1 to the ground potential. The diode LD1 flashes on; simultaneously the voltage at point "A" drops to about the opening voltage of LD1, whereby the voltage decreases slowly also at point "C" of the capacitor C20. The immediate switch-back of the comparator 15d is attained by increasing the hysteresis of the comparator by the positive feedback of the resistor $R_{39}$. The switching results in a low frequency sound signal and a light signal before the measuring section 11a.

We claim:

1. Apparatus for the determination and digital display of the position in the tooth channel of root treating means, comprising a saliva suction device, means for sensing the variation of the impedance between the saliva suction device and the root treating means, means for amplifying the variations in said impedance, means for converting said amplified variations into a DC voltage, a plurality of light displays actuated by said DC voltage, and means for varying the intensity of illumination of each of said light displays whereby the intensity of illumination of the most brightly lit said light display and the intensity of illumination of the adjacent said light displays gives a visible indication of the position of the root treating means in the tooth canal.

2. Apparatus as claimed in claim 1, and in circuit after said amplifying means a peak rectifier, a separating amplifier, and amplifiers or comparators one individual to each of the light displays for adjusting the DC voltage to a plurality of levels equal in number to the light displays, the last-named amplifiers or comparators having outputs connected to corresponding inputs of a digital decoding circuit in the form of a BCD-decimal decoder, said decoder having outputs connected to said light displays.

3. Apparatus as claimed in claim 1, and a resistor for calibrating the apparatus, means for selectively placing said resistor in circuit with said amplifying means, a socket connected to a voltage source, and a plug detachably insertable in said socket to complete a circuit between said voltage source and amplifying means and said saliva suction device and said root treating means and the body of the patient.

4. Apparatus as claimed in claim 1, and comparators adjustable to various levels corresponding to the impedance limits of the anatomical sections of the body of the patient for switching the DC voltage of a varying value, in circuit with a rectifier-amplifier whose outputs are connected to corresponding inputs of a decoding circuit in the form of a BCD-decimal decoder, said decoder having outputs connected to said light displays, said light displays having diodes of different opening voltages having a common anode, the display diode of highest opening voltage being connected in series with a diode which in turn is connected to a loudspeaker via a resistor, said loudspeaker being connected to said common anode via a capacitor and said resistor and loudspeaker being connected in parallel to a voltage source.

* * * * *